United States Patent
Bettinger et al.

(10) Patent No.: US 11,478,178 B2
(45) Date of Patent: Oct. 25, 2022

(54) ELECTRONIC STRUCTURES ON SWOLLEN HYDROGELS

(71) Applicant: Carnegie Mellon University, Pittsburgh, PA (US)

(72) Inventors: Christopher J. Bettinger, Pittsburgh, PA (US); Haosheng Wu, Santa Clara, CA (US); Congcong Zhu, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 331 days.

(21) Appl. No.: 15/373,394

(22) Filed: Dec. 8, 2016

(65) Prior Publication Data

US 2017/0156621 A1 Jun. 8, 2017

Related U.S. Application Data

(60) Provisional application No. 62/386,681, filed on Dec. 8, 2015.

(51) Int. Cl.
*A61B 5/291* (2021.01)
*A61B 5/00* (2006.01)

(52) U.S. Cl.
CPC ............ *A61B 5/291* (2021.01); *A61B 5/6833* (2013.01); *A61B 2562/04* (2013.01);
(Continued)

(58) Field of Classification Search
CPC ................ A61B 5/0478; A61B 5/6833; A61B 2562/0209; A61B 2562/04;
(Continued)

(56) References Cited

U.S. PATENT DOCUMENTS

2005/0272214 A1* 12/2005 Chiang ................. G02F 1/1523
438/309
2008/0169059 A1* 7/2008 Messersmith ............. C08J 7/12
156/249

(Continued)

FOREIGN PATENT DOCUMENTS

KR 2015055739 A * 4/2015

OTHER PUBLICATIONS

Ahn, et al., Highly Conductive and Flexible Silver Nanowire-Based Microelectrodes on Biocompatible Hydrogel, ACS Appl. Mater. Interfaces, vol. 6, pp. 18401-18407 (2014).*

(Continued)

*Primary Examiner* — Maris R Kessel
(74) *Attorney, Agent, or Firm* — Fish & Richardson P.C.

(57) ABSTRACT

This document describes a conformable substrate that includes a hydrogel having adhesion-promoting moieties, said adhesion-promoting moieties comprising one or more catechol groups. The conformable substrate includes an array of microelectrodes bonded to the hydrogel by the adhesion-promoting moieties via the one or more catechol groups. This document also describes a method for transfer printing of an electronic structure to a hydrogel. The method includes the steps of coating a donor substrate with a film of polyacrylic acid, crosslinking the film of polyacrylic acid in a solution comprising divalent ions, patterning a microelectrode array onto the crosslinked film of polyacrylic acid, laminating an adhesive hydrogel substrate onto the donor substrate coated by the crosslinked film of polyacrylic acid comprising the patterned microelectrode array, and separating the crosslinked film of polyacrylic acid from the donor substrate in a monovalent solution.

25 Claims, 12 Drawing Sheets

(52) U.S. Cl.
CPC ... *A61B 2562/125* (2013.01); *A61B 2562/164* (2013.01); *A61B 2562/166* (2013.01)

(58) Field of Classification Search
CPC ........ A61B 2562/125; A61B 2562/164; A61B 2562/166
See application file for complete search history.

(56) References Cited

U.S. PATENT DOCUMENTS

| | | | | |
|---|---|---|---|---|
| 2011/0076504 | A1* | 3/2011 | Van De Weerdt .... | C08F 220/34 428/463 |
| 2012/0078296 | A1* | 3/2012 | Lee .................. | C08G 65/33389 606/214 |
| 2012/0329882 | A1* | 12/2012 | Messersmith .......... | A61L 27/18 514/772.1 |
| 2017/0214047 | A1* | 7/2017 | Naito .................... | H01M 4/667 |

OTHER PUBLICATIONS

J. Sedo, et al., Catechol-Based Biomimetic Functional Materials, Adv. Mater. 2013, vol. 25, pp. 653-701.*
A. Sánchez-Iglesias, et al., Highly Transparent and Conductive Films of Densely Aligned Ultrathin Au Nanowire Monolayers, Nano Lett., vol. 12, pp. 6066-6070 (2012.*
K. Kang et al., Electrochemically Driven, Electrode-Addressable Formation of Functionalized Polydopamine Films for Neural Interfaces, Angew. Chem. Int. Ed., vol. 51, pp. 13101-13104 (2012).*
Lee, S., Inoue, Y., Kim, D. et al. A strain-absorbing design for tissue-machine interfaces using a tunable adhesive gel. Nat Commun 5, 5898 (2014). (Year: 2014).*
S.R. Forrest, "The Path to ubiquitous and low-cost organic electronic appliances on plastic," *Nature* 2004, 428, 911-8.
H. Yan et al., "A high-mobility electron-transporting polymer for printed transistors,", *Nature* 2009, 457, 679-86.
C. Reese et al., "Organic thin film transistors,", *Materials Today* 2004, 7, 20-27.
Q. Cao et al., "Medium-scale carbon nanotube thin-film integrated circuits on flexible plastic substrates," *Nature* 2008, 454, 495-500.
M. Kaltenbrunner et al., "An ultra-lightweight design for imperceptible plastic electronics," *Nature* 2013, 499, 458-63.
S.P. Lacour et al., "Stretchable gold conductors on elastomeric substrates," *Appl. Phys. Lett.* 2003, 82, 2404.
F. Xu et al., "Highly stretchable carbon nanotube transistors with ion gel gate dielectrics," *Nano Lett.* 2014, 14(2), 682-6.
C.J. Bettinger, Z. Bao, "Organic thin-film transistors fabricated on resorbable biomaterial substrates," *Adv. Mater.* 2010, 22(5), 651-5.
S.W. Hwang et al., "High-performance biodegradable/transient electronics on biodegradable polymers," *Adv. Mater.* 2014, 26(23), 3905-11.
M. Irimia-Vladu, "Green" electronics: biodegradable and biocompatible materials and devices for sustainable future, *Chem. Soc. Rev.* 2014, 43(2), 588-610.
Z.-Q, Lin et al., "Supramolecular Materials," *Adv. Mater.* 2013, 25, 3663.
C. Pang et al., "Highly skin-conformal microhairy sensor for pulse signal amplification," *Adv. Mater.* 2015, 27(4), 634-40.
T. Someya et al., "A large-area, flexible pressure sensor matrix with organic field-effect transistors for artificial skin applications," *Proc. Natl. Acad. Sci. USA* 2004, 101(27), 9966-70.
M. Irimia-Vladu et al., "Biocompatible and Biodegradable Materials for Organic Field-Effect Transistors," *Adv. Funct. Mater.* 2010, 20, 4069-4076.
L. Yin et al., "Materials, designs, and operational characteristics for fully biodegradable primary batteries," *Adv. Mater.* 2014, 26(23), 3879-84.
A. R. Lingley et al., "A single-pixel wireless contact lens display," *J. Micromech. Microeng.* 2011, 21, 125014.

J. Pandey et al., "A Fully Integrated RF-Powered Contact Lens With a Single Element Display," *IEEE Trans. Biomed. Circuits Syst.* 2010, 4(6), 454-61.
H. Yao et al., "A contact lens with embedded sensor for monitoring tear glucose level," *Biosens. Bioelectron.* 2011, 26(7), 3290-6.
D. J. Lipomi et al., "Skin-like pressure and strain sensors based on transparent elastic films of carbon nanotubes," *Nat. Nanotechnol.* 2011, 6(12), 788-92.
D.H, Kim et al., "Epidermal electronics," *Science* 2011, 333(6044), 838-43.
L. Xu et al., "3D multifunctional integumentary membranes for spatiotemporal cardiac measurements and stimulation across the entire epicardium," *Nat. Comms.* 2014, 1-10.
H.J. Chung et al., "Stretchable, multiplexed pH sensors with demonstrations on rabbit and human hearts undergoing ischemia," *Adv. Healthc Mater.* 2014, 3(1), 59-68.
Y. M. Song et al., "Digital cameras with designs inspired by the arthropod eye," *Nature* 2013, 497, 95-99.
S.P. Lacour et al., "Flexible and stretchable micro-electrodes for in vitro and in vivo neural interfaces," *Med. Biol. Eng. Comput.* 2010, 48(10), 945-54.
I.R. Minev et al., "Biomaterials. Electronic dura mater for long-term multimodal neural interfaces," *Science* 2015, 347(6218), 159-63.
S. Wagner, S. Bauer, "Materials for stretchable electronics," *MRS Bull.* 2012, 37, 207-213.
C. Hassler, T. Boretius, T. Stieglitz, "Polymers for Neural Implants," *J Polym. Sci., Part B: Polym. Phys.* 2011, 49, 18-33.
H. Zhang et al., "Tissue-compliant neural implants from microfabricated carbon nanotube multilayer composite," *ACS Nano* 2013, 7(9), 7619-29.
S. Atzet et al., "Degradable poly(2-hydroxyethyl methacrylate)-co-polycaprolactone hydrogels for tissue engineering scaffolds," *Biomacromolecules* 2008, 9(12), 3370-7.
S. Sekine, "Conducting polymer electrodes printed on hydrogel," *J Am. Chem. Soc.* 2010, 132(38), 13174-5.
H. Ding et al., "Biologically Derived Soft Conducting Hydrogels Using Heparin-Doped Polymer Networks," *ACS nano* 2014, 8, 4348-4357.
Y. Ido et al., "Conducting Polymer Microelectrodes Anchored to Hydrogel Films," *ACS Macro Letters* 2012, 1,400-403.
Y. Ahn et al., "Highly conductive and flexible silver nanowire-based microelectrodes on biocompatible hydrogel," *ACS Appl. Mat. Interfaces* 2014, 6(21), 18401-7.
M.S. Mannoor et al., "3D printed bionic ears," *Nano Lett.* 2013, 13(6),2634-9.
J.O. You, D.T. Auguste, "Conductive, physiologically responsive hydrogels," *Langmuir* 2010, 26(7), 4607-12.
M. M. Ling, Z. Bao, "Thin Film Deposition, Patterning, and Printing in Organic Thin Film Transistors," *Chem. Mater.* 2004, 16, 4824-4840.
Y.L. Loo et al., "Interfacial chemistries for nanoscale transfer printing," *J Am. Chem. Soc.* 2002, 124(26), 7654-5.
Y.-L. Loo et al., "Additive, nanoscale patterning of metal films with a stamp and a surface chemistry mediated transfer process: Applications in plastic electronics," *Appl. Phys. Lett.* 2002, 81, 562.
D. R. Hines et al., "Transfer printing methods for the fabrication of flexible organic electronics," *J Appl. Phys.* 2007, 101, 024503.
A. Carlson et al., "Transfer printing techniques for materials assembly and micro/nanodevice fabrication," *Adv. Mater.* 2012, 24(39), 5284-318.
B. P. Lee et al., "Mussel-Inspired Adhesives and Coatings," *Annu. Rev. Mater. Res.* 2011, 41:99-132.
J.H. Waite, "Mussel power," *Nat. Mater.* 2008, 7(1), 8-9.
J.H. Waite, "Reverse engineering of bioadhesion in marine mussels," *Ann. N.Y Acad. Sci.* 1999, 875, 301-9.
P. Glass et al., "Enhanced reversible adhesion of dopamine methacrylamide-coated elastomer microfibrillar structures under wet conditions," *Langmuir* 2009, 25(12), 6607-12.
K.C. Black et al., "Catechol Redox Induced Formation of Metal Core-Polymer Shell Nanoparticles," *Chem. Mater.* 2011, 23(5), 1130-1135.
H. Lee et al., "Single-molecule mechanics of mussel adhesion," *Proc. Natl. Acad. Sci. U.S.A.* 2006, 103(35), 12999-3003.

(56) References Cited

OTHER PUBLICATIONS

B.K. Ahn et al., "Surface-initiated self-healing of polymers in aqueous media,", *Nat. Mater.* 2014, 13(9), 867-72.
B.D. Ratner, S.J. Bryant, "Biomaterials: where we have been and where we are going," *Annu. Rev. Biomed. Eng.* 2004, 6, 41-75.
A. J. Cadotte, T.B. DeMarse, "Poly-HEMA as a drug delivery device for in vitro neural networks on micro-electrode arrays," *J Neural Eng.* 2005, 2(4), 114-22.
R. Langer et al., "Biocompatibility of polymeric delivery systems for macromolecules," *J Biomed. Mater. Res.* 1981, 15(2), 267-77.
C. Alvarez-Lorenzo et al., "Soft contact lenses capable of sustained delivery of timolol," *J Phann. Sci.* 2002, 91(10), 2182-92.
A. Opdahl et al., "Surface mechanical properties of pHEMA contact lenses: viscoelastic and adhesive property changes on exposure to controlled humidity," *J Biomed. Mater. Res. Part A* 2003, 67(1), 350-6.
T.V. Chirila, "An overview of the development of artificial corneas with porous skirts and the use of PHEMA for such an application," *Biomaterials* 2001, 22(24), 3311-7.
J. K. Park et al., "Facile Surface Modification and Application of Temperature Responsive Poly(N-isopropy-lacrylamide-co-dopamine methacrylamide)," *Macromol. Chem. Phys.* 2012, 213, 2130-2135.
P. Ramesh, S. Sampath, "Electrochemical and spectroscopic characterization of quinone functionalized exfoliated graphite," Analyst 2001, 126(11), 1872-7.
C. Berthomieu et al., "Characterization by FTIR spectroscopy of the photoreduction of the primary quinone acceptor QA in photosystem II," *FEBSLett.* 1990,269(2), 363-7.
Z.I. Kalcioglu et al., "Tunable mechanical behavior of synthetic organogels as biofidelic tissue simulants," *J Biomech.* 2013, 46(9), 1583-91.
M.A. Green et al., "In vivo brain viscoelastic properties measured by magnetic resonance elastography," *NMR Biomed.* 2008, 21(7), 755-64.
S. Nicolle et al., "Shear Properties of Brain Tissue over a Frequency Range Relevant for Automotive Impact Situations: New Experimental Results," *Stapp Car Crash J* 2004, 48, 239-58.
S. Skelton et al., "Biomimetic adhesive containing nanocomposite hydrogel with enhanced materials properties," *Soft Matter* 2013, 9, 3825-3833.
B. P. Lee et al., "Modulating the movement of hydrogel actuator based on catechol-iron ion coordination chemistry," *Sens. Actuators, B* 2015, 206, 456-462.
M. Shen et al., "Rheology and adhesion of poly(acrylic acid)/laponite nanocomposite hydrogels as biocompatible adhesives," *Langmuir* 2014, 30(6), 1636-42.
L. Bromberg et al., "Bioadhesive properties and rheology of polyether-modified poly(acrylic acid) hydrogels," *Int. J. Phann.* 2004, 282(1-2), 45-60.
X. Feng et al., "Competing fracture in kinetically controlled transfer printing," *Langmuir* 2007, 23(25), 12555-60.
S. Kim et al., "Enhanced adhesion with pedestal-shaped elastomeric stamps for transfer printing," *Appl. Phys. Lett.* 2012, 100, 171909.
S. Kim et al., "Microstructured elastomeric surfaces with reversible adhesion and examples of their use in deterministic assembly by transfer printing," *Proc. Natl. Acad. Sci. USA* 2010, 107(40), 17095-100.
B. P. Lee et al., "Rapid Gel Formation and Adhesion in Photocurable and Biodegradable Block Copolymers with High DOPA Content," *Macromolecules* 2006, 39, 1740-1748.
C.E. Brubaker, P.B. Messersmith, "Enzymatically degradable mussel-inspired adhesive hydrogel," *Biomacromolecules* 2011, 12(12), 4326-34.
G. M. Mullen et al., "The Effects of Adsorbed Water on Gold Catalysis and Surface Chemistry," *Top. Catal* 2013, 56, 1499-1511.
R. L. Wells, T. Fort, "Adsorption of Water on Clean Gold by Measurement of Work Function Changes," 1972, 32, 554-560.
M. Weinhold et al., "Structure and bonding of the multifunctional amino acid L-DOPA on Au(110)," *J. Phys. Chem. B* 2006, 110(47), 23756-69.
H. Chung et al., "Enhanced adhesion of dopamine methacrylamide elastomers via viscoelasticity tuning," *Biomacromolecules* 2010, 12(12), 342-7.
P. Tseng et al., "Flexible and stretchable micromagnet arrays for tunable biointerfacing," *Adv. Mater.* 2015, 27(6), 1083-9.
V. Linder et al., "Water-soluble sacrificial layers for surface micromachining," *Small* 2005, 1(7), 730-6.
R. Agarwal et al., "Scalable imprinting of shape-specific polymeric nanocarriers using a release layer of switchable water solubility," *ACS Nano* 2012, 6(3), 2524-31.
I. M. Graz et al., "Silicone substrates with in situ strain relief for stretchable thin-film transistors," *Appl. Phys. Lett.* 2011, 98, 124101.
S. P. Lacour et al., "Deformable interconnects for conformal integrated circuits," *Proc. Mater. Res. Soc. Symp.* 2002, 736, D4.8.1-D4.8.6.
D.Y. Khang et al., "A stretchable form of single-crystal silicon for high-performance electronics on rubber substrates," *Science* 2006, 311(5758), 208-12.
J. Xiao et al., "Stretchable and compressible thin films of stiff materials on compliant wavy substrates," *Appl. Phys. Lett.* 2008, 93, 013109.
J.A. Rogers et al., "Materials and mechanics for stretchable electronics," *Science* 2010, 327(5973), 1603-7.
D.Gulsen, A. Chauhan, "Ophthalmic drug delivery through contact lenses," *Invest. Ophthalmol. Vis. Sci.* 2004, 45(7), 2342-7.
C. Cvetkovic et al., "Three-dimensionally printed biological machines powered by skeletal muscle," *Proc. Natl. Acad. Sci. USA* 2014, 111(28), 10125-30.
B. P. Lee, S. Konst, "Novel hydrogel actuator inspired by reversible mussel adhesive protein chemistry," *Adv. Mater.* 2014, 26(21), 3415-9.
C. Keplinger et al., "Stretchable, transparent, ionic conductors," *Science* 2013, 341(6149), 984-7.
S. Naficy et al., "Electrically Conductive, Tough Hydrogels with pH Sensitivity," *Chem. Mater.* 2012, 24, 3425-3433.
T. M. Higgins et al., "Gellan gum doped polypyrrole neural prosthetic electrode coatings," *Soft Matter* 2011, 7, 4690.
L. Pan et al., "Hierarchical nanostructured conducting polymer hydrogel with high electrochemical activity," *Proc. Natl. Acad. Sci. USA* 2012, 109(24), 9287-92.
H. Lee et al., "A reversible wet/dry adhesive inspired by mussels and geckos," *Nature* 2007, 448(7151), 338-41.

\* cited by examiner

ELECTRONIC STRUCTURES ON SWOLLEN HYDROGELS

CLAIM OF PRIORITY

This application claims priority under 35 USC § 119(e) to U.S. Patent Application Ser. No. 62/386,681 filed on Dec. 8, 2015, the entire contents of which are hereby incorporated by reference.

GOVERNMENT RIGHTS

This invention was made with government support under Contract Number D14AP00040 awarded by the Defense Advanced Research Projects Agency. The government has certain rights in the invention.

BACKGROUND

It is useful to integrate electronic structures onto flexible substrates for flexible electronics. However, direct integration of microelectronics with swollen hydrogel substrates is challenging with commonly available microfabrication techniques such as photolithography and transfer printing. Hydrated networks prohibit vacuum-based thin-film deposition techniques directly on hydrogel substrates. High swelling ratios and hydrated surface environments of the hydrogel substrates also attenuate van der Waals interactions, which are used for transfer printing of prefabricated microelectronics. Furthermore, most elastomeric substrates used in flexible electronics have Young's moduli ranging from 0.2-2 MPa, orders of magnitude larger than the modulus of many excitable organs including the heart and brain. The mechanical mismatch at the biotic-abiotic interface may damage local cell populations due to acute insults and micro-motion artifacts. The resulting tissue responses prohibit stable chronic device operation and tissue integration.

SUMMARY

This document describes application-specific target hydrogel substrates for electronic structures. Additionally, this document describes processes for transfer printing of electronic structures to swollen hydrogels. The adhesion-promoting hydrogels and transfer printing processes are made possible through the design and synthesis of the adhesion-promoting hydrogels as target substrates. This document describes fabrication techniques that advance ultracompliant electronics by melding microfabricated structures with swollen hydrogel substrates.

In some implementations, the conformable substrate includes a hydrogel having adhesion-promoting features, such as moieties comprising one or more catechol groups. In some implementations, the catechol groups are presented by a monomer, such as domaine methacrylate. In some implementations, other functionalities achieve adhesion such as dopamine acrylates, polydopamine films or networks, and so forth. The conformable substrate further comprises an array of microelectrodes bonded to the hydrogel by the adhesion-promoting features or moieties, such as the one or more catechol groups.

The catechol group is bonded to the microelectrodes using one or more of aromatic groups, hydrogen bonds, and coordination bonds. The hydrogel includes one or more of poly 2-hydroxyethyl methacrylate and polyethyleneglycol. The hydrogel includes a dopamine methacrylamide monomer.

In some implementations, the hydrogel includes a precursor solution photocrosslinked into a film. The precursor solution includes a P(HEMA-co-DMA) precursor solution having approximately 86.8 mol/mol % HEMA and 10.7 mol/mol % DMA. The precursor solution includes a P(HEMA) precursor solution having approximately 97.5 mol/mol % HEMA. The film includes a thickness in a range of 100 nanometers to 10 millimeters. The microelectrodes include a gold layer having a thickness of approximately 30 nanometers. The microelectrodes have an approximate width of 2 mm, a length of 200 μm, and are spaced from each other by a spacing of 100 μm.

In some implementations, at least 98% of the microelectrodes comprise a crack-free morphology. In some implementations, the hydrogel has a swelling ratio of greater than 4.85. In some implementations, the resistance of at least one microelectrode of the array of microelectrodes is between 10 and 15 ohms.

In some implementations, at least one microelectrode of the array of microelectrodes includes a strain-relief geometrical design that reduces strain effects from swelling of the hydrogel. The strain-relief geometrical design includes a serpentine design.

In some implementations, the hydrogel forms a contact lens. In some implementations, the hydrogel forms a conformal sensor for measuring EEG. In some implementations, the hydrogel forms an electrochemical sensor. In some implementations, the hydrogel forms a laminated sensor for monitoring cardiac activity. In some implementations, the hydrogel forms a sensor/stimulation combination for use with stimulating/monitoring cells cultured on hydrogel-based substrates.

In some implementations, the microelectrodes comprise one or more of metal conductors, ceramics, polymers, semiconductors, or insulators.

In some implementations a process for transfer printing microelectronics into a hydrogel substrate includes coating a donor substrate with a film of polyacrylic acid, crosslinking the film of polyacrylic acid in a solution comprising divalent ions, patterning a microelectrode array onto the crosslinked film of polyacrylic acid, laminating an adhesive hydrogel substrate onto the donor substrate coated by the crosslinked film of polyacrylic acid comprising the patterned microelectrode array, and separating the crosslinked film of polyacrylic acid from the donor substrate in a monovalent solution.

In some implementations, the patterning includes one or more of photolithography, electrodeposition, or nanoimprinting. In some implementations, the microelectrode array includes gold and the patterning includes thermal evaporation through shadow masks. In some implementations, 99.5% or more of microelectrodes of the microelectrode array are transferred to the hydrogel during the laminating and the separating.

In some implementations, the actions include forming the adhesive hydrogel substrate from a P(HEMA) precursor solution having approximately 97.5 mol/mol % HEMA. In some implementations, the actions include forming the adhesive hydrogel substrate from a P(HEMA-co-DMA) precursor having 86.8 mol/mol % HEMA and 10.7 mol/mol % DMA. In some implementations, laminating includes compressing the donor substrate into the adhesive hydrogel substrate without external heat or pressure and while submerged in water.

In some implementations, a process for transfer printing microelectronics into a hydrogel substrate includes coating a silicon substrate with a film of polyacrylic acid, wherein the film of polyacrylic acid is water-soluble; crosslinking the film of polyacrylic acid in a $CaCl_2$ solution comprising $Ca^{2+}$ ions; patterning an array of gold microelectrodes onto the crosslinked film of polyacrylic acid by thermal evaporation, wherein the microelectrodes have a width of 2 mm, a length of 200 μm, and spacing of 100 μm, and wherein a thickness of the microelectrodes is 30 nm; laminating, onto the silicon substrate, a P(HEMA-co-DMA) hydrogel substrate, the silicon substrate coated by the crosslinked film of polyacrylic acid comprising the patterned array; separating the crosslinked film of polyacrylic acid from the silicon substrate in a NaCl solution.

The application-specific target hydrogel substrates and transfer printing processes described herein provide several advantages. Polymeric substrates are an important component in flexible electronics because they can overcome many limitations associated with inorganic substrates that may be rigid, brittle, and planar. Devices fabricated on polymeric substrates can also be light weight, stretchable, or biodegradable. These systems are suitable for applications including environmentally friendly sensors, wearable medical devices, and temporary biomedical implants. For example, contact lenses can be impregnated with electronics to improve visual acuity or measure glucose levels in real time.

Dissolvable and elastomeric substrates allow conformal coating of sensor arrays with curvilinear organs such as the skin, eye, heart, and brain. Devices that interface with excitable cells will benefit from substrate materials that are highly compliant to promote conformal contact and reduce the risk of damaging delicate tissue. Hydrogel-based materials can improve the sensing and stimulation of excitable tissue by promoting conformal integration of electronic devices and bridging the abiotic-biotic interface.

Multi-electrode arrays fabricated on ultrathin poly(ethylene terephthalate) substrates use polyrotoxane hydrogel films to improve tissue-device integration while monitoring cardiac function in vivo. Hydrogels can serve as templates for in-situ assembly of metallic nanoparticles through metal ion reduction or conducting polymers via oxidative polymerization.

DETAILED DESCRIPTION

The present invention includes an application-specific target hydrogel substrate for transfer printing of electronic microstructures. This approach utilizes hydrogels with adhesion-promoting moieties that permit direct assembly of functional microstructures on swollen target hydrogel substrates via transfer printing. This technique melds thin film patterning and deposition techniques with adhesive highly compliant swollen hydrogel substrates.

Adhesion in hydrated environments is a challenging problem that has been solved in part by recent discoveries of adhesion-promoting catechol-bearing materials. Catechols bond to inorganic/organic materials in hydrated environments through polarizable aromatic groups, hydrogen bonds, and coordination bonds. Hydrogels synthesized from non-toxic poly(2-hydroxyethyl methacrylate) (P(HEMA)) and polyethyleneglycol precursors are materials that are employed in biomedical devices used in human trials for many applications including controlled release matrices, soft contact lenses, and artificial corneas. Catechol-bearing HEMA-based hydrogels are suitable target substrates for transfer printing of electronic structures.

Figure 1A:
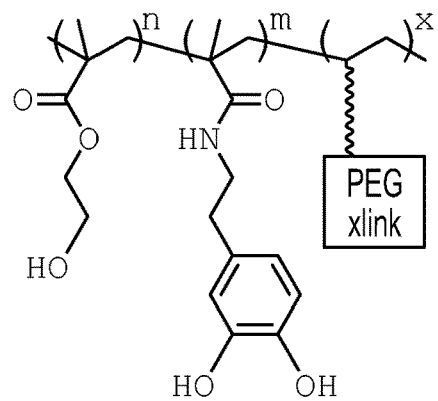
FIG. 1A shows an example chemical structure of P(HEMA-co-DMA).

Turning to FIG. 1A, a chemical structure of P(HEMA-co-DMA) is shown. Dopamine methacrylate (DMA) monomers are copolymerized with HEMA hydrogels and poly (ethyl glycol) dimethacrylate crosslinker to form P(HEMA-co-DMA) hydrogels. Other monomers besides dopamine methacrylate are suitable for presenting the catechol that functions as the adhesive component. In some implementations, the catechol bearing monomer can include dopamine acrylates, polydopamine films, polydomaine networks, and so forth.

Figure 1B:
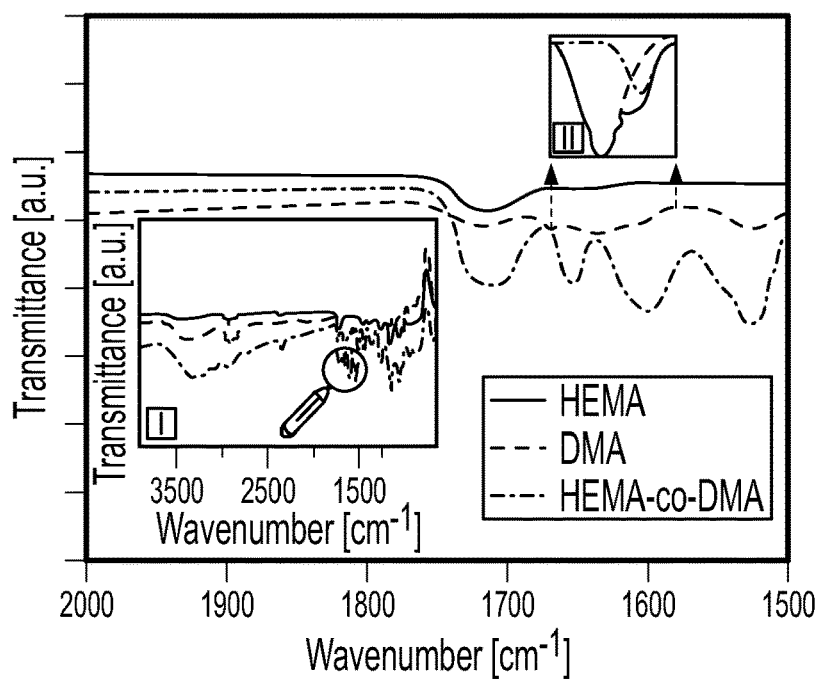
FIG. 1B is a graph showing FT-IR spectra of the DMA monomer, dehydrated P(HEMA) and P(HEMA-co-DMA) hydrogel networks.

DMA incorporation was characterized using Fourier Transform Infrared Spectroscopy (FT-IR) (e.g., as seen in FIG. 1B). FT-IR spectra of the DMA monomer, dehydrated P(HEMA) and P(HEMA-co-DMA) hydrogel networks indicates the incorporation of DMA with two characteristic peaks highlighted at 1602 and 1523 $cm^{-1}$. The inset (i) shows a full spectrum of FT-IR from 4000-400 $cm^{-1}$. Inset (ii) shows a deconvoluted spectra (dash lines) of the original spectrum (solid line) from 1600 to 1650 $cm^{-1}$ of P(HEMA-co-DMA)). DMA monomers exhibit strong peaks at 1523 and 1653 $cm^{-1}$, which are assigned to N—H bending in amides and C=C bonds in pendant methacrylates, respectively. The latter peak is abolished after P(HEMA-co-DMA) hydrogel formation through crosslinking via photopolymerization. Peak deconvolution of features from 1600 to 1650 $cm^{-1}$ of P(HEMA-co-DMA) indicates that C—C stretches at 1602 $cm^{-1}$ from aromatic rings in DMA are preserved in P(HEMA-co-DMA) hydrogels. The new peak at 1633 $cm^{-1}$ in P(HEMA-co-DMA) is assigned to C=O bonds associated with possible catechol oxidation into quinone during free radical photopolymerization.

Figure 1C:
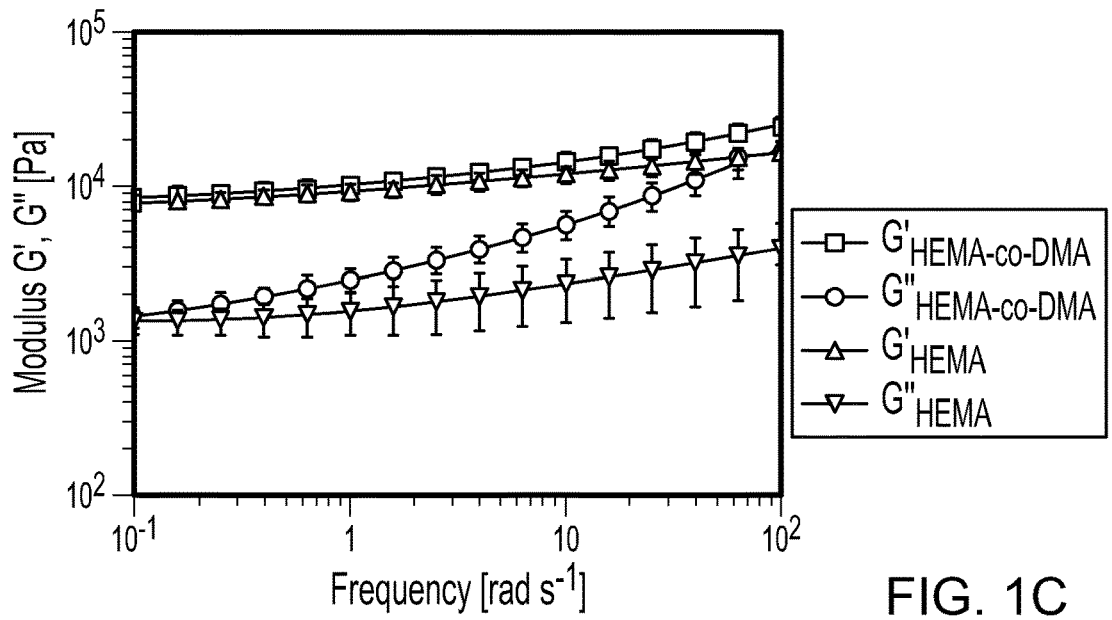
FIG. 1C is a graph showing storage G' and loss G" moduli of both P(HEMA-co-DMA) and P(HEMA) hydrogel substrates.

Turning to FIG. 1C, the storage G' and loss G" moduli of both P(HEMA-co-DMA) and P(HEMA) hydrogel substrates are shown with a frequency swept between 0.1 and 100 rad $s^{-1}$ under constant 2% strain. P(HEMA-co-DMA) hydrogels with a 10:1.23 ratio of HEMA to DMA exhibit a storage modulus $G'_{HEMA-co-DMA}=8.2\pm1.2$ kPa ($\omega=0.1$ rad $s^{-1}$), which is comparable to the storage modulus of P(HEMA) at the same frequency $G'_{HEMA}=7.7\pm0.7$ kPa.

Both $G'_{HEMA-co-DMA}$ and $G'_{HEMA}$ are largely frequency independent. The value of $G'_{HEMA-co-DMA}$ increases to 24.4±4.6 kPa at $\omega=100$ rad $s^{-1}$ while $G'_{HEMA}$ increases to 16.5±2.8 kPa. These values match the range of storage moduli of excitable tissues such as those located in the heart and brain.

Values for $G'_{HEMA-co-DMA}$ are also slightly larger than $G'_{HEMA}$ at all frequencies. Both HEMA and DMA monomers can participate in intra- and intermolecular H-bonding via pendant hydroxyl groups and esters/amides, respectively. The observation that $G'_{HEMA-co-DMA}>G'_{HEMA}$ can be attributed to DMA groups that both reduce chain rotation and form physical crosslinks via π-π stacking. The loss modulus $G''_{HEMA-co-DMA}$ for P(HEMA-co-DMA) hydrogels exhibits a stronger frequency dependence compared to $G''_{HEMA}$ such that $G''_{HEMA-co-DMA}>2G''_{HEMA}$ at the frequency regime of ω>5 rad $s^{-1}$. This observation could be attributed to DMA groups in swollen P(HEMA-co-DMA) hydrogels that form transient physical crosslinks through π-π stacking that can be ruptured at high frequencies. The viscoelastic behavior of P(HEMA-co-DMA) hydrogels described herein is consistent with previous reports of catechol-bearing hydrogels. Taken together, the mechanical properties of P(HEMA) hydrogels are largely preserved despite incorporating DMA.

The adhesion between Au films and either catechol-bearing P(HEMA-co-DMA) or control P(HEMA) hydrogels was measured via uniaxial indentation with both Au and hydrogel surfaces fully submerged in water. Au is an ideal material for integration with hydrogel substrates for prospective biomedical applications because it is electronically conductive and corrosion resistant. In some implementations, a mix of other conductive metals, ceramics, polymers, semiconductors, and insulators is used for the electronic structures. Au is also an important test case for adhesive hydrogels because it is chemically inert and does not form covalent bonds with catechol-bearing moieties. Adhesion experiments were performed by coating a planar rigid indenter with a thin layer of Au and placing it in contact with hydrogels at a constant maximum preload for a fixed amount of time. Force-distance curves were then recorded as the indenter is retracted from the hydrogel.

Figure 2A:
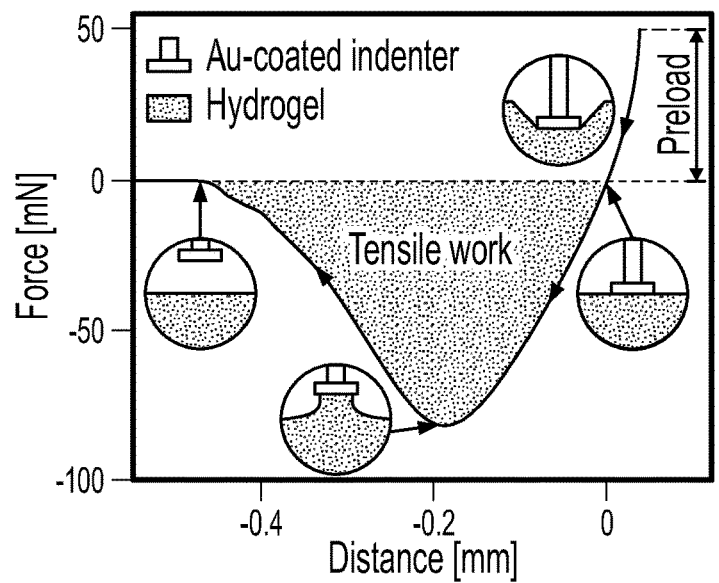
FIG. 2A is a graph showing a representative force-distance curve.
Figure 2B:
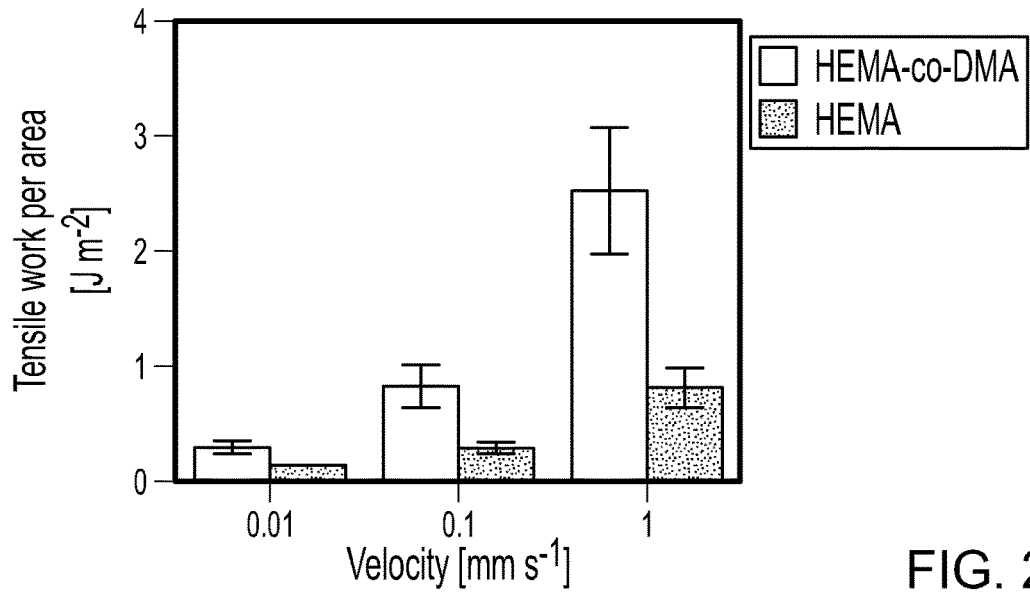
FIGS. 2B-2C are graphs showing values for extracted tensile work per area for hydrogels.
Figure 2C:
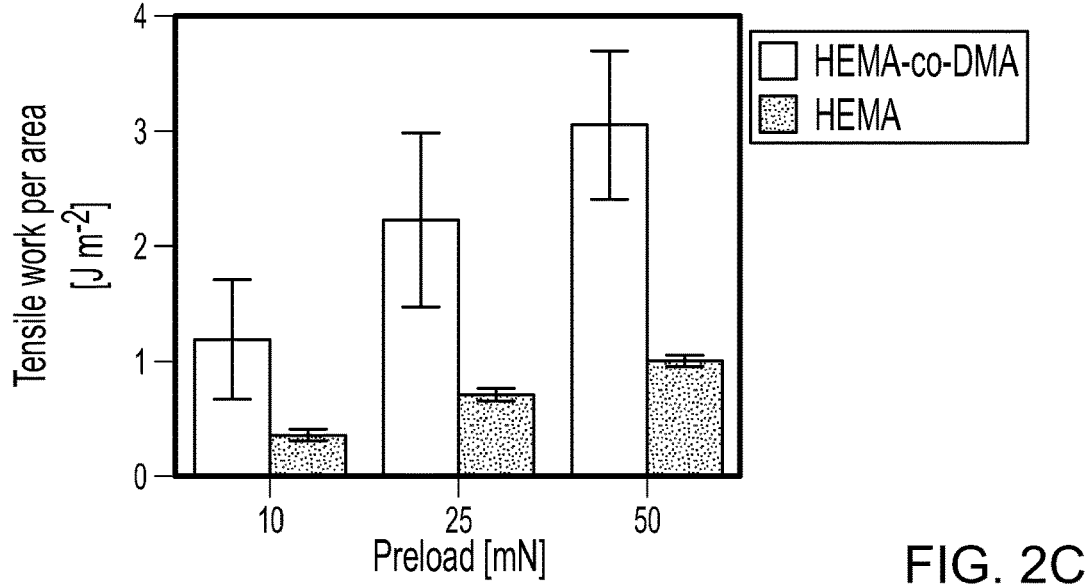

Turning to FIGS. 2A-2C, the shaded area of the force-distance curve represents the tensile work needed to overcome the interfacial adhesion and delaminate the Au-coated indenter completely from the hydrogel. FIG. 2A shows a representative force-distance curve recorded when retracting the Au-coated indenter from the P(HEMA-co-DMA) surface at a constant speed of 0.1 mm $s^{-1}$ after 5 minutes' contact at a constant preload of 50 mN. The shaded area indicates the tensile work needed to fully delaminate the indenter from the hydrogel surface. FIG. 2B shows values for extracted tensile work per area $W_{gel-Au}$ with constant preload of 50 mN and varied retracting velocity from 0.01-1 mm $s^{-1}$. FIG. 2C shows values for extracted $W_{gel-Au}$ with constant retracting velocity 1 mm $s^{-1}$ and varied preloads from 10-50 mN that indicate the marginal surface adhesion increase in P(HEMA-co-DMA) versus P(HEMA) hydrogels.

The speed of delamination influences the interfacial adhesion and is an important parameter in engineering transfer printing processes. Representative force-distance curves and the extracted tensile work per unit area $W_{gel-Au}$ are shown for each hydrogel substrate composition as a function of retraction speed (See FIGS. 8 and 2B). Both P(HEMA) and P(HEMA-co-DMA) hydrogels exhibit rate-dependent adhesion where $W_{gel-Au}$ is positively correlated with retraction speed. This observed trend is attributed to the viscoelastic nature of the hydrogels. Catechol-bearing P(HEMA-co-DMA) hydrogels with the 10:1.23 ratio of HEMA to DMA significantly increase the value of $W_{gel-Au}$ compared to P(HEMA) ($W_{HEMA-co-DMA-Au}$~3 $W_{HEMA-Au}$) for retraction speeds ranging from 10 μm $s^{-1}$ to 1 mm $s^{-1}$. Comparable increases in surface adhesion have been reported in other catechol-bearing hydrogel networks.

The improved adhesion described above could be attributed to several types of bonds between the hydrogel substrates and Au films. Although not wishing to be bound by theory, one possible mechanism for increased adhesion of P(HEMA-co-DMA) hydrogels to Au films is hydrogen bond formation between catechols and adsorbed water on Au surfaces. P(HEMA) can form similar bonds via pendent hydroxyl groups from HEMA monomers. Highly polarizable aromatic groups in DMA may bond to Au films through charge transfer or π-π stacking. The material dampening as measured by tan $(\delta_{HEMA-co-DMA})$ is >10% higher compared to tan $(\delta_{HEMA})$ at an angular frequency $\omega=0.2$ rad $s^{-1}$, as shown in FIG. 1C. This value roughly corresponds to the maximum retraction velocity v=1 mm $s^{-1}$. These data suggest that P(HEMA-co-DMA) dissipates more energy through viscous responses compared to P(HEMA) hydrogel substrates and therefore requires relatively more tensile work for delamination. The observed relationship of $W_{HEMA-co-DMA-Au}$~3 $W_{HEMA-Au}$ could be due to increased interfacial bonding and viscous dissipation in catechol-bearing hydrogels. The values of $W_{HEMA-co-DMA-Au}$ and $W_{HEMA-Au}$ were also measured as a function of preload force, as shown in FIG. 2C. The measured value of $W_{HEMA-co-DMA-Au}$ is larger than $W_{HEMA-Au}$ for all preload conditions.

Figure 3:
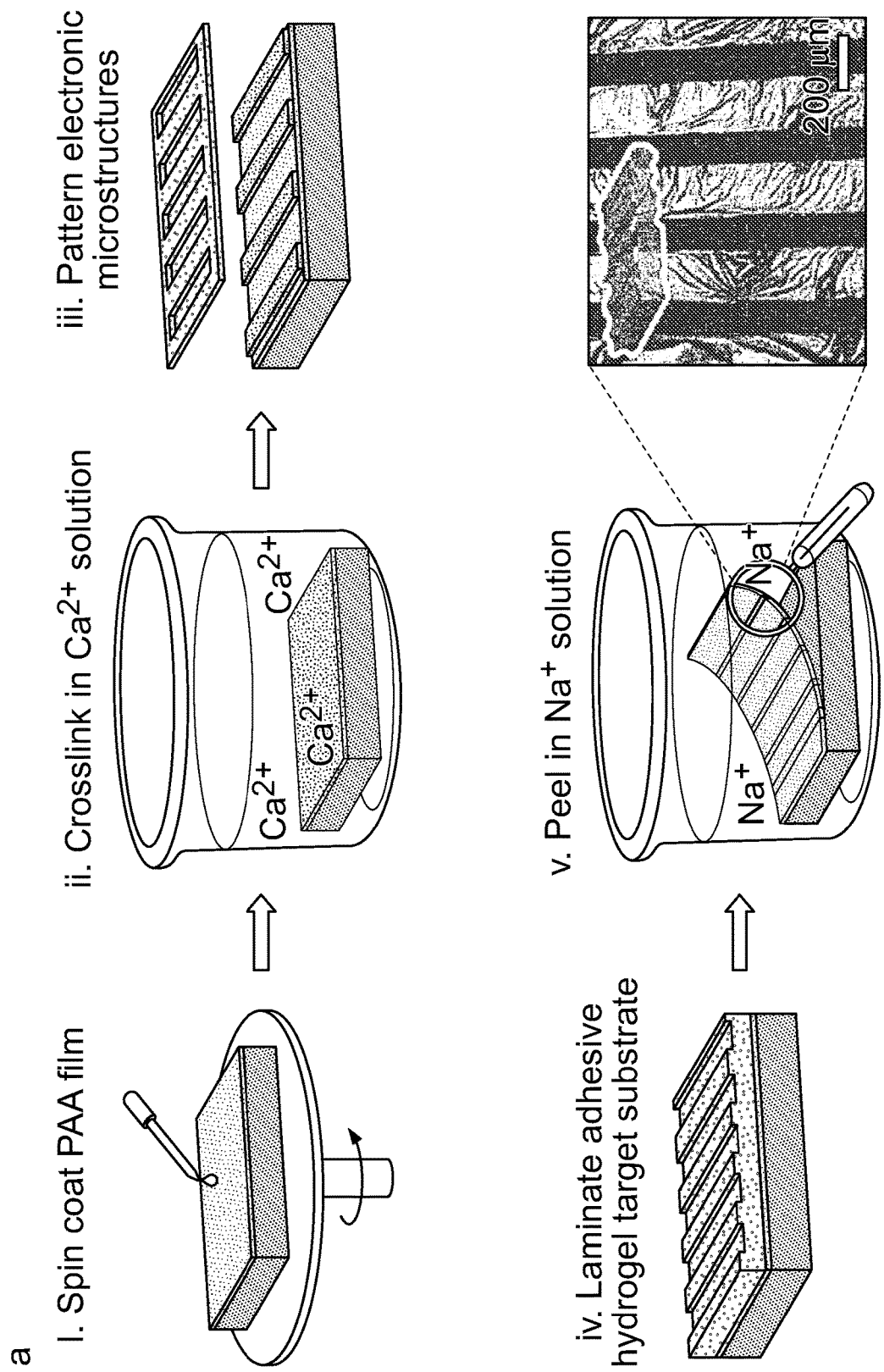
FIG. 3 shows an example process for transfer printing electronic structures onto a hydrogel.

As seen in FIG. 3, Au microstructures are transferred to adhesive P(HEMA-co-DMA) hydrogel substrates using a modified transfer printing process. Donor substrates for transfer printing are prepared by (a-i) spin-coating a sacrificial layer of water-soluble PAA and (a-ii) crosslinking in CaCl solution prior to (a-iii) fabricating Au microelectrodes on PAA-Ca2 surfaces. An adhesive swollen P(HEMA-co-DMA) target substrate is conformably laminated (a-iv) on the donor substrate surface for 5 minutes and (a-v) removed from the donor substrate in NaCl solution to transfer the Au microelectrodes onto the hydrogel substrate. The optical micrograph shows a portion of the Au microelectrode array on the hydrogel substrates.

A donor substrate was coated with a sacrificial layer of water-soluble poly(acrylic acid) (PAA), which has 89.8±5.2 nm in thickness. Water stable PAA films were formed through ionic crosslinking with divalent $Ca^{2+}$ ions. Sacrificial ionically crosslinked PAA films are compatible with the microfabrication of superpositioned inorganic microstructures by photolithography, electrodeposition, and nanoimprinting. Au microelectrode arrays were patterned on PAA-$Ca^{2+}$ coated substrates by thermal evaporation through shadow masks. Au microelectrodes with thicknesses of ~30 nm are commonly employed for electrodes and interconnects because this dimension preserves stretchability in Au thin films. PAA-$Ca^{2+}$ films are stable during conformal lamination of swollen P(HEMA-co-DMA) hydrogels.

Figure 9:
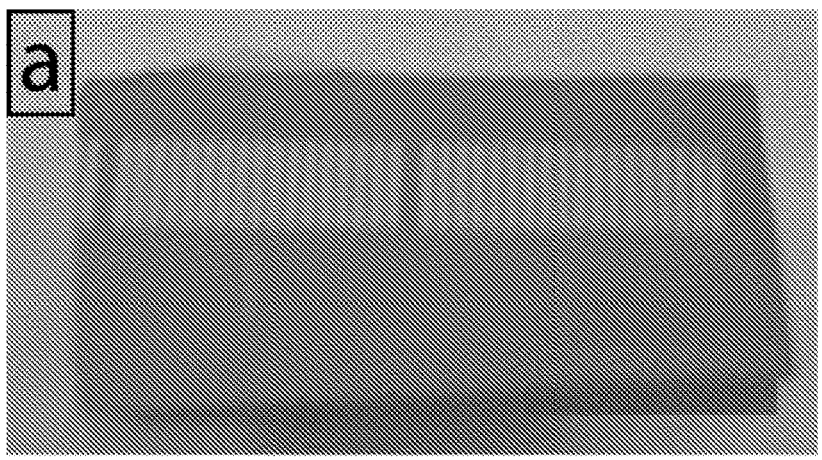
FIGS. 9A-9C are representative macroscopic images showing transfer printing of AU microelectrode arrays from donor substrates onto hydrogel target substrates.
Figure 9:
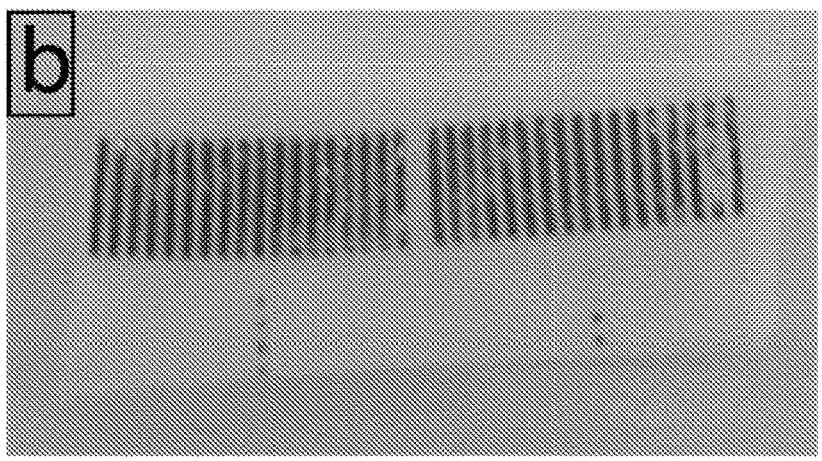
Figure 9:
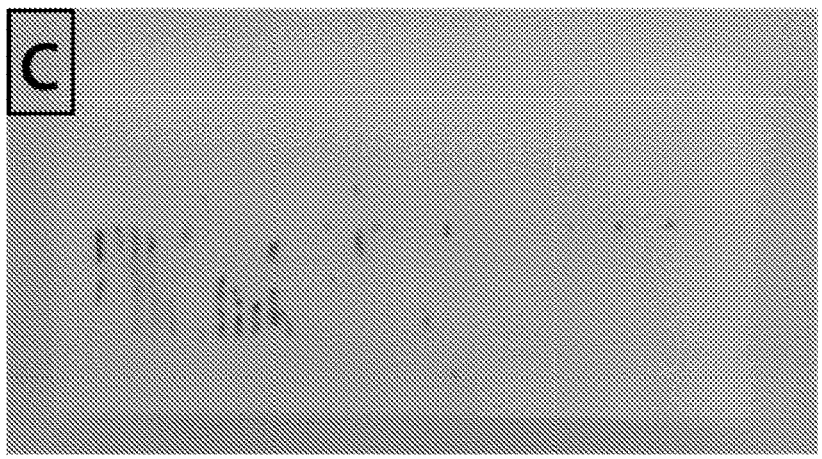

FIGS. 9A-9C show representative macroscopic images showing transfer printing of Au microelectrode arrays. FIG. 9A shows PAA-$Ca^{2+}$/Si donor substrates transferred to adhesive P(HEMA-co-DMA) hydrogel target substrates (See FIG. 9B). FIG. 9C shows P(HEMA) hydrogel substrates. The transfer yield of P(HEMA-co-DMA) target substrates was significantly larger compared to P(HEMA). Scale bars all represent 0.5 mm.

Figure 6:
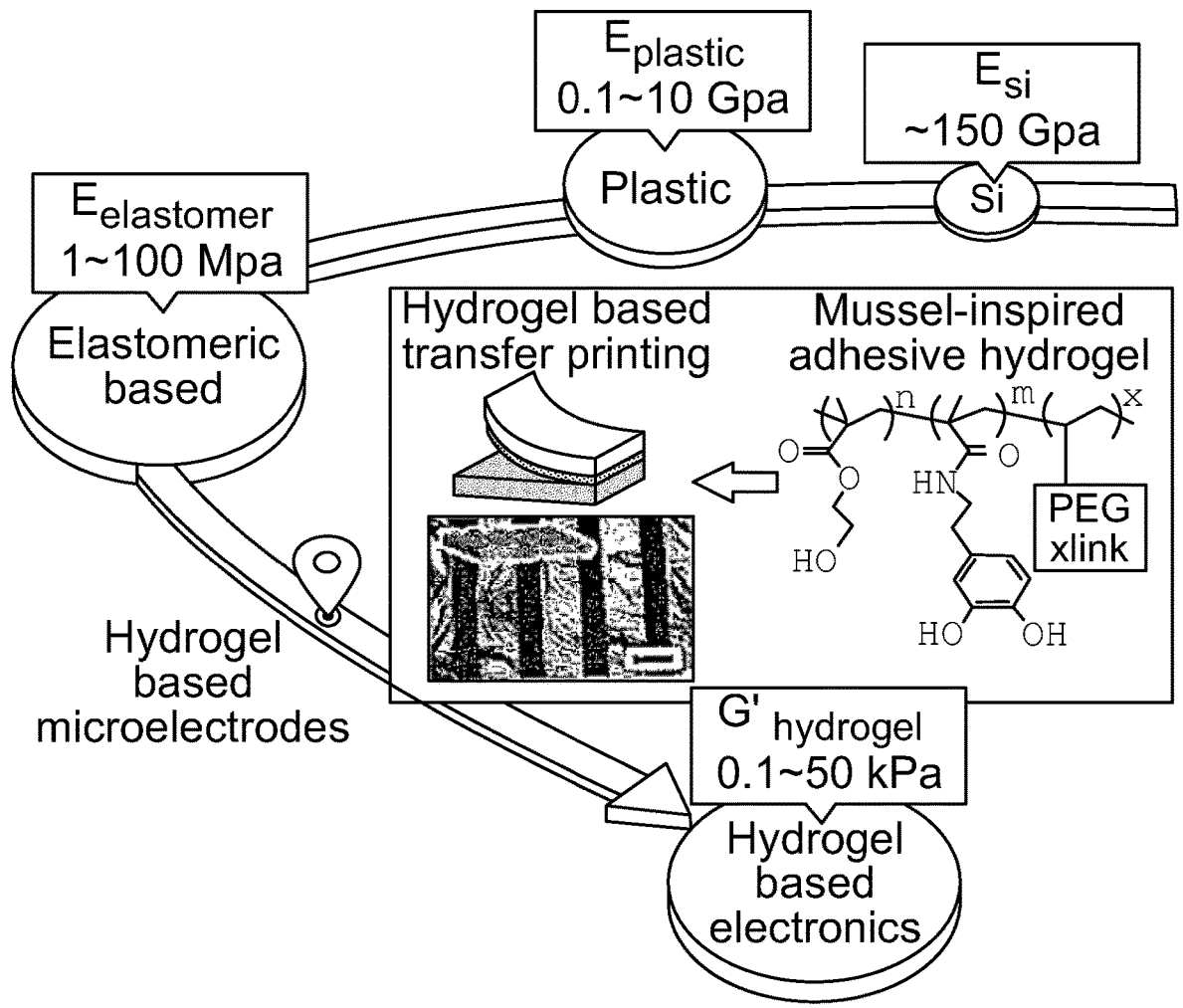
FIG. 6 is a diagram showing a comparison of substrates for electronic structures.

Sacrificial PAA-$Ca_2$ films eliminated non-specific adhesion between the hydrogel and the donor substrate, thereby preserving integrity of target hydrogel substrates and increasing the yield of transferred microstructures. Dissolution of sacrificial PAA-$Ca_2$ layers by monovalent cation exchange promoted separation of adhesive P(HEMA-co-DMA) target substrates from donor substrates. Au microstructures can be transferred from Si donor substrates to swollen P(HEMA-co-DMA) hydrogel target substrates (10:1.23 ratio of DMA to HEMA) with yields (>99.5% as measured by the total area ratio of ($A_{\mu electrodes, target}$/$A_{\mu electrodes, donor}$) that are significantly higher compared to P(HEMA) target substrates (<20%), as shown in FIGS. 9A-9C. Au microelectrodes adopt a buckled, but largely crack-free morphology (~98% microstructures are crack free) after being transferred to target P(HEMA-co-DMA) hydrogel substrates. Buckled features form due to the modulus mismatch between the Au thin film and the hydrogels in addition to transient deformation of hydrogels during transfer printing. FIG. 6 shows a comparison of different substrates for microelectronic structures.

Figure 4:
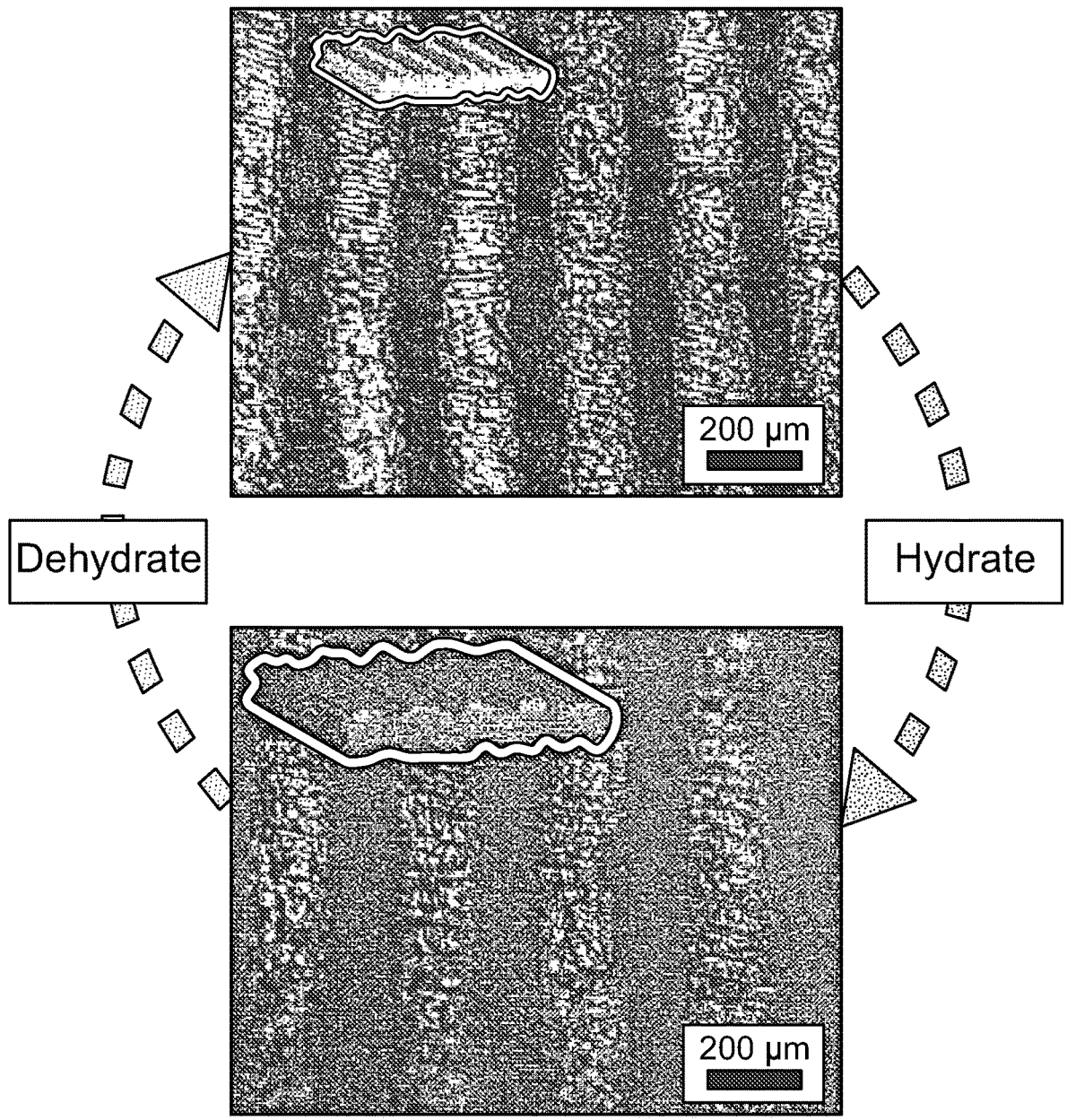
FIG. 4 are images showing optical micrographs of Au microelectrode arrays.
Figure 5:
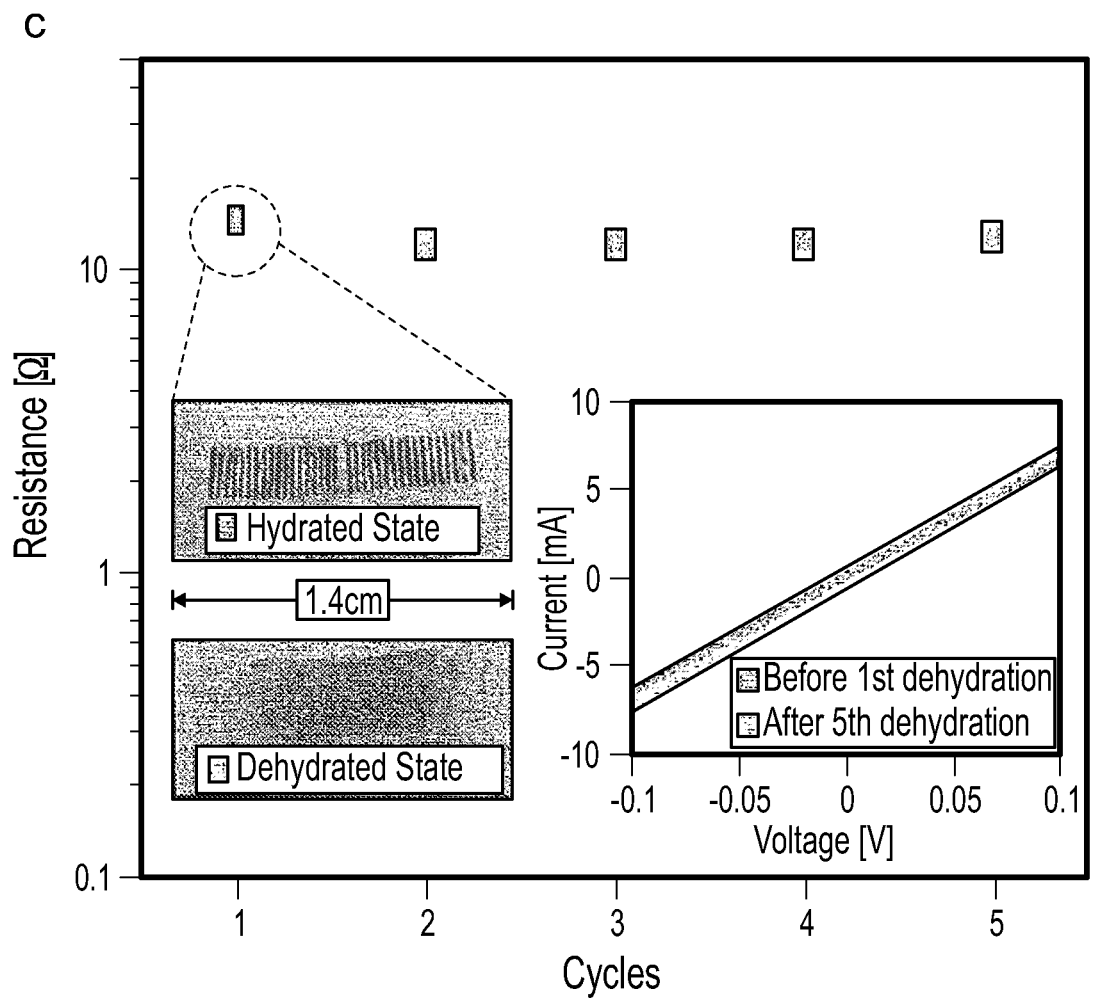
FIG. 5 is a graph showing values for extracted resistance of Au microelectrodes.

FIG. 4 shows optical micrographs of Au microelectrode arrays when the P(HEMA-co-DMA) substrate is cycled between hydrated and dehydrated states. As seen in FIG. 5, values for extracted resistance of Au microelectrodes (n=8) indicate the electrical conductivity is preserved for 5 hydration/dehydration cycles. The inset shows the linear current-voltage characteristic of the Au microelectrodes before $1^{st}$ dehydration and after the $5^{th}$ dehydration.

Buckled microstructures may be beneficial by increasing the maximum permissible strain of electrically conductive films. Au microstructures adhered to P(HEMA-co-DMA) hydrogel substrates during cycles of hydration and dehydration (FIG. 3b). P(HEMA-co-DMA) hydrogels have a swelling ratio of $Q=(m_{swollen}/m_{dry})_{n=1}=4.89\pm0.22$ where n is the hydration/dehydration cycle number. Dimensional swelling can be calculated via $(L_{swollen}/L_{dry})_{n=1}=Q^{1/3}=1.70\pm0.02$ assuming isotropic swelling. Dimensional swelling is reduced for cycles n>1 via $(L_{swollen}/L_{dry})_{n=1, avg.}=1.63\pm0.05$. The decrease in the dimensional swelling after the first cycle is likely due to the formation of additional physical crosslinks between pendant catechol groups during the first dehydration cycle. The swelling ratio is measured either gravimetrically or from changes in volume of the hydrogel.

Figure 10:
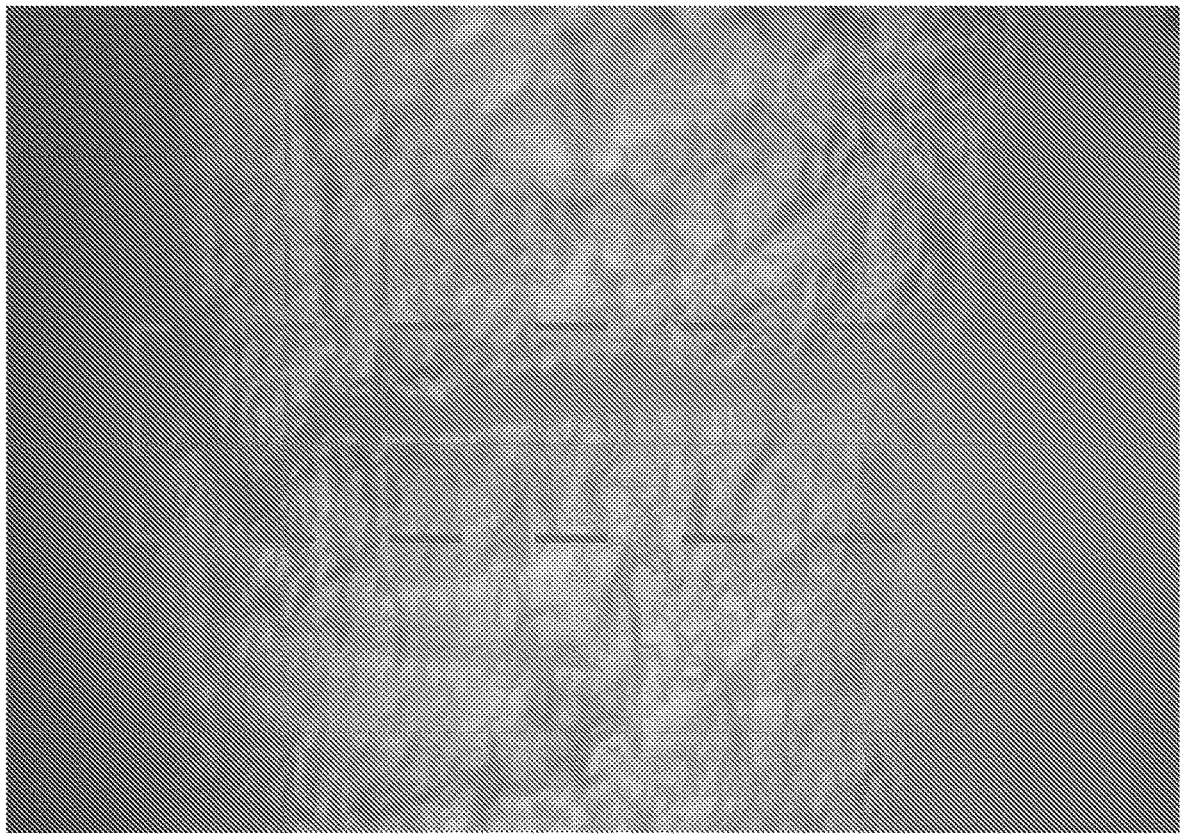
FIG. 10 is an optical micrograph showing the formation of microcracks in a microelectrode.

As shown in FIG. 5, the resistance of Au microelectrodes was measured using two-probe current-voltage measurements. The end-to-end resistance $R_{Au}$ of the as-transferred Au microelectrode was calculated to be 14.9±1.1 Q prior to the first dehydration. As shown in FIG. 5, the electrical conductivity of Au microelectrodes on P(HEMA-co-DMA) hydrogels is largely constant for hydration/dehydration cycles for up to n=5 ($R_{Au}$=12.8±0.7Ω for the dehydrated state of n=5). For cycles n>5, no delamination of the Au microelectrodes was observed, which indicates the adhesion between the Au thin film and P(HEMA-co-DMA) hydrogel substrate is preserved. As shown in FIG. 10, minor fissures in some microelectrodes form due to fatigue, which could be potentially relieved by incorporating strain-relief designs such as the serpentine patterns into the microelectrode geometry.

Hydrogel-based electronics afford unique advantages compared to devices fabricated on flexible and stretchable substrates for certain biomedical applications. Microfabricated electrode arrays in which inorganic structures are integrated with highly compliant hydrogels permit electrophysiological monitoring of excitable tissues in native mechanical environments. Electronically active structures fabricated on HEMA-based polymer networks also lead to the next-generation of smart contact lenses capable of diagnostic and therapeutic functions. Other applications include conformal sensors for measuring EEG, electrochemical sensors, laminated sensors for monitoring cardiac activity, or other sensor/stimulation combinations for use with stimulating/monitoring cells cultured on hydrogel-based substrates.

FIG. 10 shows an optical micrograph shows the formation of microcracks (indicated by regions with dashed lines) in the microelectrode at the hydrated state of 61 hydration/dehydration cycles. Scale bar represents 50 mm.

Figure 11:
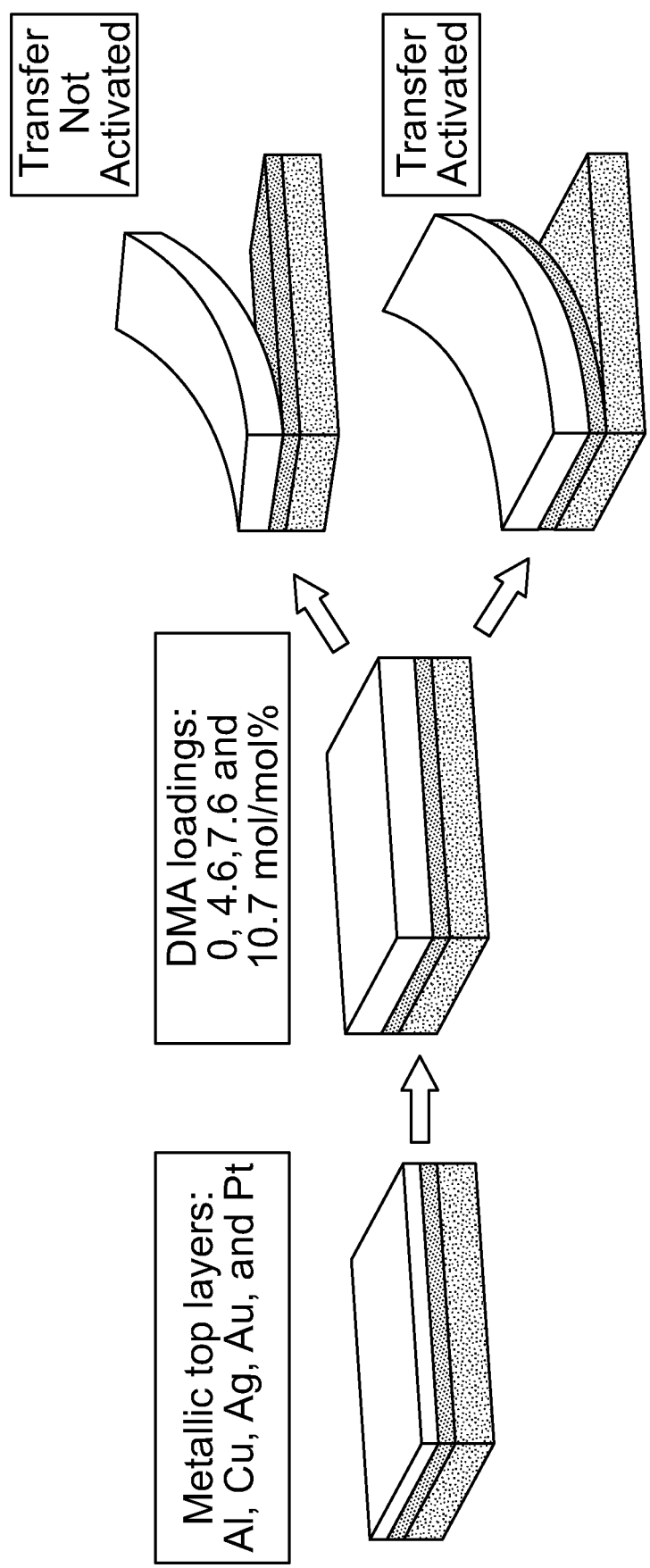
FIG. 11 shows composition-dependent transfer printing of various metals with P(HEMA-co-DMA) hydrogels of varying DMA concentrations.
Figure 12:
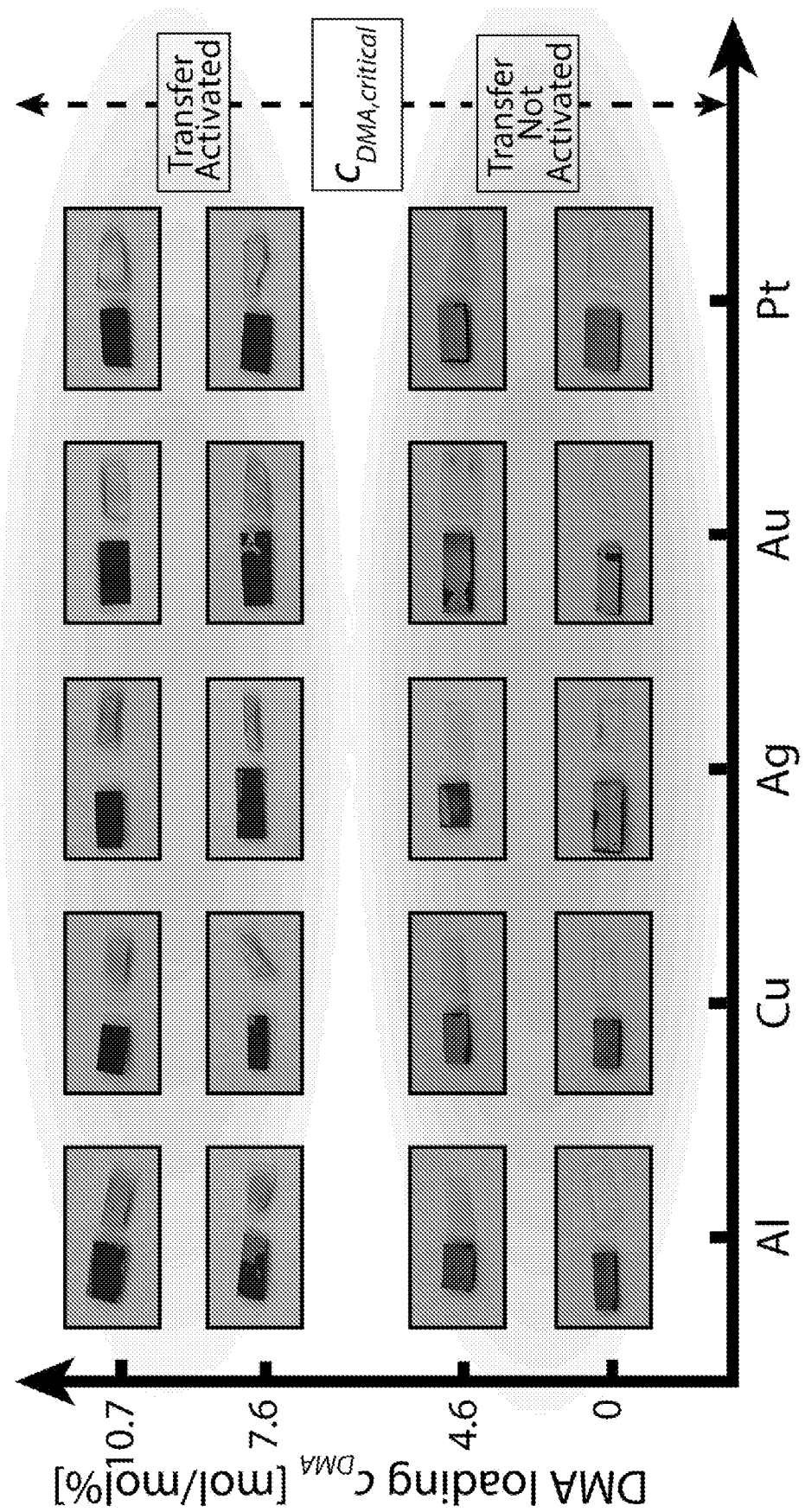
FIG. 12 is a graph showing transfer printing results.

As shown in FIGS. 11-12, catechol-bearing P(HEMA-co-DMA) target hydrogel substrates also exhibit increased adhesion with many film compositions, which is promising for fabricating devices with multiple materials. Functional devices fabricated on hydrogels facilitate integration of electronic structures with tissue through minimally invasive procedures. The fabrication strategy of the present invention melds swollen hydrogel substrates with conventional vacuum-based device microfabrication techniques for potential applications in soft bio-hybrid robots, actuators, and mixed charge conducting media.

FIG. 11 shows composition-dependent transfer printing of various metals with P(HEMA-co-DMA) hydrogels of varying DMA concentrations. Bi-layer metallic thin films are composed of 10 nm of a metal film laminated to a 40 nm bottom layer composed of Au. The composition of the top layers included Al, Cu, Ag, Au, and Pt. Al, Cu, Ag and Au films are deposited on $SiO_2$/Si substrate surfaces by thermal evaporation while Pt films are formed by sputtering. The 40 nm Au bottom layer was used to ensure that all bi-layer thin films have same adhesion values $W_{Au-SiO2}$ with the donor substrate.

P(HEMA-co-DMA) are prepared with DMA loadings $c_{DMA}$ including 0, 4.6, 7.6, 10.7 mol/mol % while total monomer concentrations of HEMA and DMA were held constant at 97.5 mol/mol %. P(HEMA-co-DMA) hydrogel substrates were laminated on donor substrates and kept in contact for 5 minutes before gradual delamination.

FIG. 12 shows macroscopic images including the transfer printing results with $SiO_2$/Si donor substrates placed on the left and P(HEMA-co-DMA) target substrates placed on the right. The transfer printing results indicate transfer printing yields increase with increasing DMA loadings.

P(HEMA-co-DMA) with 10.7 mol/mol % DMA can transfer bi-layer metallic films of any composition with yields higher than 99% (areal coverage). The critical DMA concentrations such that $C_{DMA, critical}$ ($W_{HEMA-co-DMA-metal}$) $C_{DMA, critical} \approx W_{Au-SiO2}$ occurs between 4.6-7.6 mol/mol %. P(HEMA-co-DMA) hydrogels with $C_{DMA}$<5 mol/mol % cannot transfer metallic films of any composition to target substrates. Macroscopic images show hydrogel substrates in the dehydrated state. Defects shown in the Au+0 mol/mol % DMA case are caused by the fixation clapping during thin film deposition.

In some implementations, the target hydrogel substrates are prepared as described below. Dopamine hydrochloride is prepared as described above to produce catechol-bearing monomer dopamine methacrylamide (DMA). Briefly, dopamine-HCl (26.4 mmol) is reacted with methacrylate anhydride (29.1 mmol) in 25 ml of tetrahydrofuran. The pH of the solution is kept above 8 during the reaction by adding 1 M NaOH dropwise as necessary. In some implementations, the solution is washed with ethyl acetate, combined with hexane, and held at 4° C. for 18 hr.

Figure 7:
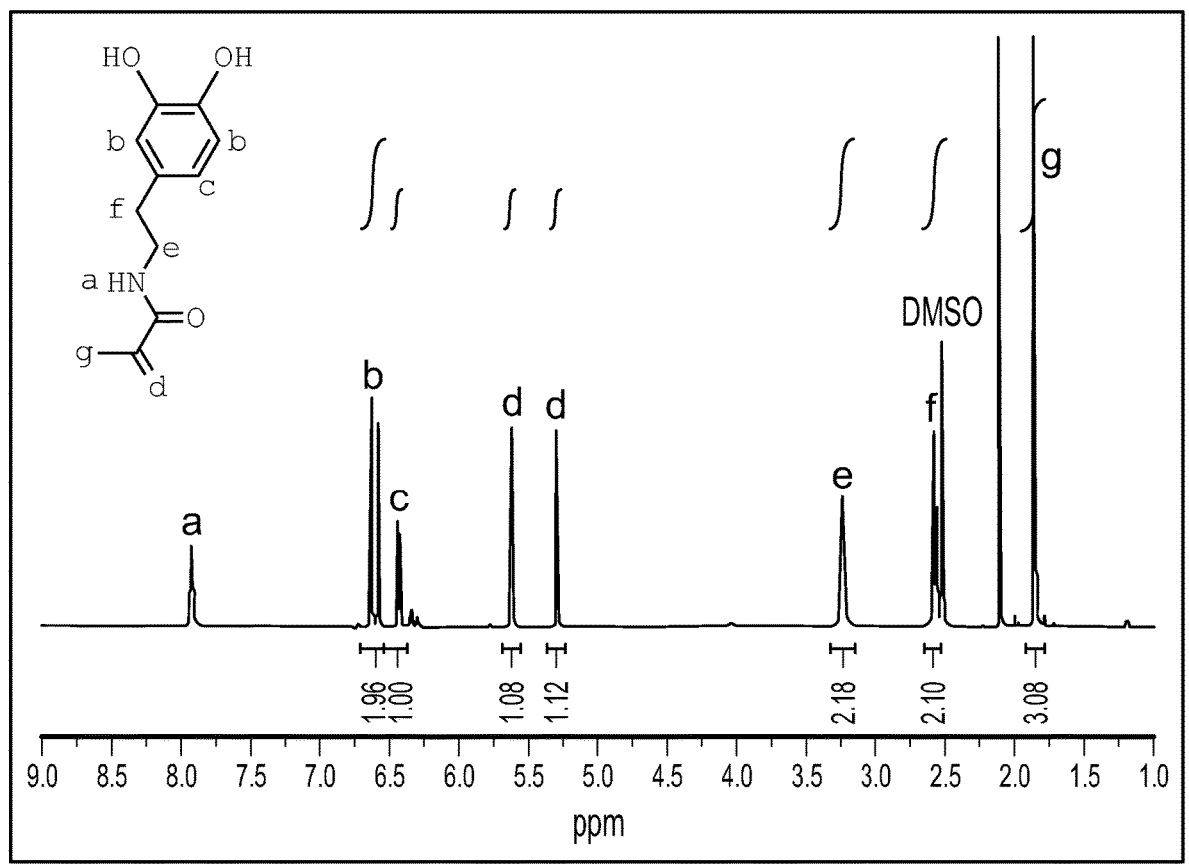
FIG. 7 is a chart showing a $^1H$ NMR spectrum of a DMA monomer.

As shown in FIG. 7, purified DMA can be analyzed using $^1$H nuclear magnetic resonance. In some implementations, hydrogel precursors including monomers 2-hydroxyethyl methacrylate (HEMA) and DMA, crosslinker polyethyleneglycol dimethacrylate (PEGDMA, Mw=1000) as well as photoinitator 2-hydroxy-4'-(2-hydroxyethoxy)-2-methylpropiophenone (Irgacure 2959) are dissolved in a 1.88 mL solvent mixture containing 79.8% deionized water (DI H2O) and 20.2% dimethyl sulfoxide to yield a solution with a total precursor concentration of 1.58 M.

In some implementations, P(HEMA-co-DMA) hydrogels contain 86.8 mol/mol % HEMA, 10.7 mol/mol % DMA, 1.7 mol/mol % PEGDMA, and 0.8 mol/mol % Irgacure 2959. In some implementations, precursor solutions for P(HEMA) hydrogels contain 97.5 mol/mol % HEMA, 1.7 mol/mol % PEGDMA, and 0.8 mol/mol % Irgacure 2959. In some implementations, other ratios are possible. For example, any ratio is possible as long as the molar ratio of catechol groups (e.g., dopamines) exceeds 5 mol/mol %. In some implementations, the solution can include 5 mol % DMA to 50 mol % DMA or more. Hydrogel precursor solutions are photocrosslinked into films 1 mm in thickness using Teflon coated glass slides at 600 mW/cm$^2$ UVB lamp for >60 sec. Hydrogels are equilibrated in DI H$_2$O for 24 hours after photocrosslinking. In some implementations, the films can be a thickness in the rage of 100 nm to 10 mm. In some implementations, compositions of hydrogels having at least 5 mol % catechol concentrations can be used.

Microelectrode fabrication on donor substrates can include several processes. In some implementations, Si/SiO$_2$ donor substrates are cleaned using a sequence of acetone, isopropanol, and DI H2O solvents followed by UV ozone. Poly(acrylic acid) sodium salt solution (PAA-Na$^+$) (M$_w$–31,000-50,000) is diluted in DI H$_2$O to a concentration of 5% (w/v). PAA-Na+ solution was spin coated on donor substrates at 3000 rpm for 40 seconds to form sacrificial release layers. In some implementations, donor substrates are annealed at 150° C. for 2 min and treated with 5 M CaCl$_2$ solution for 5 min. Au microelectrodes (nominal length=200 µm, width=2 mm, and spacing between two adjacent electrodes=100 µm) can be patterned on sacrificial layers by thermal evaporation using shadow masks (Au thickness=30 nm, 0.2 A s$^{-1}$. Other configurations of microelectrode arrays are possible, such as alternative thicknesses, spacing, and length or width according to design preferences.

Transfer printing of thin-film structures to target hydrogel substrates can include several processes. Target hydrogel substrates are conformably laminated onto the donor substrates surface. In some implementations, the donor substrates surface remains in contact for 5 minutes without external heat or pressure. Hydrogel substrates were delaminated from donor substrates in 1 M NaCl solution.

The chemo-mechanical characterization of hydrogel target substrates can be measured as described below. Fourier transform infrared (FTIR) spectra of dehydrated gels were recorded for wavenumbers from 4000-400 cm$^{-1}$. In some implementations, the mechanical properties of hydrogels are measured using a rheometer. Adhesion measurements utilize cylindrical swollen hydrogels (h=1 mm, D=20 mm) that were mounted on a polystyrene petri dish using cyanoacrylate adhesive and submerged in 4 mL of DI H$_2$O. Flat cylindrical glass windows (D=5 mm) are coated with metallic bilayers composed of Cr/Au (5 nm, 30 nm; 0.2 A s$^{-1}$) by thermal evaporation. In some implementations, the indenter can be mounted on a 250 g load cell attached to a stack of a vertical motorized stage for indentation and two manual tilting stages for controlling the alignment. Custom-made software controls the motorized stage, while recording the measured loads at a 1 kHz sampling rate.

In each experiment, the indenter was preloaded against the hydrogel sample with forces between 10-50 mN and the software controlled the stage as needed to maintain a constant preload for a fixed contact time of 5 min. The indenter was then retracted with a constant speed between 10 mm s$^{-1}$-1 mm s$^{-1}$ and force-distance curves were recorded. The actual measured preloads deviated slightly from the nominal values due to the effects of buoyancy (~1 mN). The actual measured preloads deviated slightly from the nominal values due to the effects of buoyancy (~1 mN). The actual measured preloads deviated slightly from the nominal values due to the effects of buoyancy (~1 mN). The effect of capillary force interactions is negligible under the complete submerged conditions of adhesion measurements.

Figure 8:
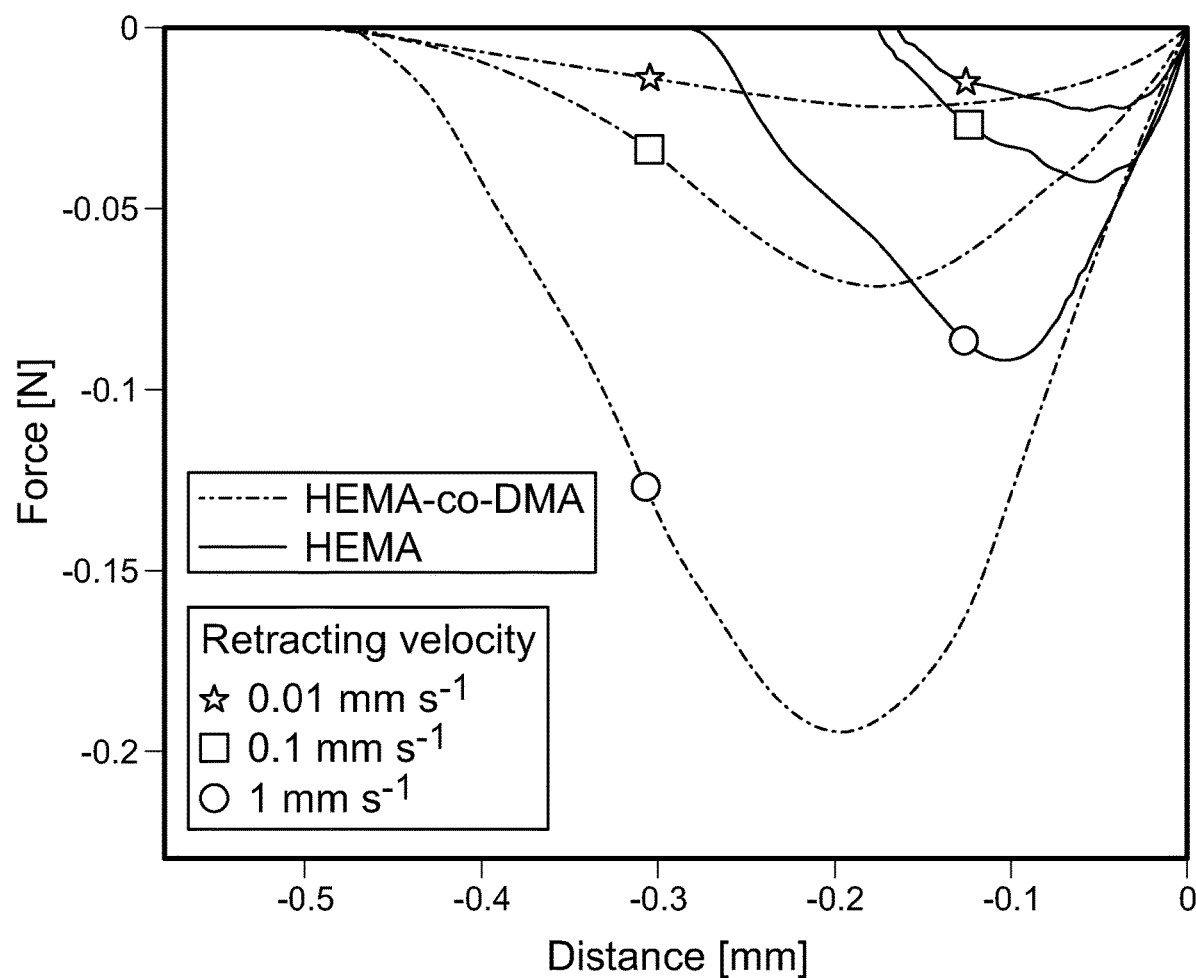
FIG. 8 is a graph showing representative force-distance curves of both P(HEMA-co-DMA) and P(HEMA) hydrogels.

FIG. 8 shows representative force-distance curves of both P(HEMA-co-DMA) and P(HEMA) hydrogels when retracting the Au-coated indenter at different velocity values including 0.01, 0.1, and 1 mm s$^{-1}$. At the same retracting speed, adhesive P(HEMA-co-DMA) hydrogels show both larger tensile work and higher maximum tensile force for the delamination between the indenter and the hydrogel surface compared to P(HEMA) controls.

The thin-film microstructure can include one, several, or all of the following characteristics. The I-V characteristics and resistance of the Au microelectrodes on adhesive hydrogels are measured using two-probe measurement in ambient conditions using an S-1160A probe station equipped with SE-TL tungsten probe tips bonded with soft Au wire (25 mm diameter and a source measuring unit (2400 SMU). During cycles of hydration/dehydration, the adhesive hydrogel substrates are dehydrated under 1 bar vacuum for ~12 hours to reach the dehydrated state and then rehydrate in DI H$_2$O for ~12 hours to reach the hydrate state. Optical micrographs are recorded using an Olympus BH2 microscope. All data presented as mean±s.d. unless otherwise stated.

Other embodiments are within the scope and spirit of the description claims. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the techniques described herein.

What is claimed is:
1. A system, comprising:
 a conformable substrate comprising a hydrogel having adhesion-promoting moieties, said adhesion-promoting moieties comprising one or more catechol groups; and an array of electronic microstructures bonded to the hydrogel by the adhesion-promoting moieties via the one or more catechol groups, wherein at least two electronic microstructures, of the array of electronic microstructures, are separated from one another and are supported by the hydrogel of the conformable substrate, wherein one or more electronic microstructures, of the array of electronic microstructures bonded to the hydrogel, comprise a planar metal surface with a crack-free morphology, and wherein the array of electronic microstructures comprises a metal bilayer, wherein a first layer includes a first adhesion value for binding to the hydrogel, the first layer supporting a second layer of the metal bilayer on the hydrogel, the second layer having a different adhesion value.

2. The system of claim 1, wherein the one or more catechol groups are bonded to the array of electronic microstructures using one or more of aromatic groups, hydrogen bonds, and coordination bonds.

3. The system of claim 1, wherein the hydrogel comprises one or more of poly 2-hydroxyethyl methacrylate, polyethyleneglycol, or copolymers thereof.

4. The system of claim 1, wherein the hydrogel comprises a dopamine methacrylamide monomer.

5. The system of claim 1, wherein the hydrogel comprises one or more of a dopamine acrylate, a polydopamine film, and a polydopamine network.

6. The system of claim 1, wherein the hydrogel comprises a precursor solution crosslinked into a film.

7. The system of claim 6, wherein the precursor solution comprises a dopamine methacrylate (DMA) and poly(2-hydroxyethyl methacrylate) (P(HEMA)) P(HEMA-co-DMA) precursor solution having approximately 86.8 mol/mol % HEMA and 10.7 mol/mol % DMA.

8. The system of claim 6, wherein the precursor solution comprises a poly(2-hydroxyethyl methacrylate P(HEMA) precursor solution having approximately 97.5 mol/mol % HEMA.

9. The system of claim 6, wherein the film comprises a thickness in a range of 100 nanometers to 10 millimeters.

10. The system of claim 6, wherein the hydrogel comprises a catechol concentration of at least 5 mol %.

11. The system of claim 1, wherein electronic microstructures, of the array of electronic microstructures, each comprise a gold layer having a thickness of at least 30 nanometers.

12. The system of claim 1, wherein electronic microstructures, of the array of electronic microstructures, form microelectrodes that each have an approximate length of 200 μm, and are spaced from each other by a spacing of 100 μm.

13. The system of claim 1, wherein at least 98% of electronic microstructures, of the array of electronic microstructures, comprise a crack-free morphology.

14. The system of claim 1, wherein the hydrogel has a swelling ratio of greater than 4.85.

15. The system of claim 1, wherein a resistance of at least one electronic microstructure of the array of electronic microstructures is between 10 and 15 ohms.

16. The system of claim 1, wherein at least one electronic microstructure of the array of electronic microstructures comprises a strain-relief geometrical design that reduces strain effects from swelling of the hydrogel.

17. The system of claim 16, wherein the strain-relief geometrical design comprises a serpentine design.

18. The system of claim 1, wherein the hydrogel forms a contact lens.

19. The system of claim 1, wherein electronic microstructures, of the array of electronic microstructures, comprise one or more of metal conductors, ceramics, polymers, semiconductors, or insulators.

20. The system of claim 1, wherein the hydrogel is at least a portion of a conformal sensor for measuring electroencephalogram (EEG).

21. The system of claim 1, wherein the hydrogel is at least a portion of an electrochemical sensor.

22. The system of claim 1, wherein the hydrogel is at least a portion of a laminated sensor for monitoring cardiac activity.

23. The system of claim 1, wherein the hydrogel is at least a portion of a device configured for stimulating cells, monitoring cells, or both stimulating and monitoring cells cultured on hydrogel-based substrates.

24. The system of claim 1, wherein the at least two electronic microstructures of the array of electronic microstructures are electronically separated from one another on the hydrogel of the conformable substrate.

25. The system of claim 1, wherein a width of at least one of the electronic microstructures, of the array of electronic microstructures, is 2 millimeters.

* * * * *